United States Patent [19]
Hinds

[11] Patent Number: 5,759,036
[45] Date of Patent: Jun. 2, 1998

[54] COMPLETE DENTAL IMPLANT SYSTEM AND METHOD

[76] Inventor: Kenneth F. Hinds, 4 Costa Del Sol, Monarch Beach, Calif. 92629

[21] Appl. No.: 681,699

[22] Filed: Jul. 29, 1996

[51] Int. Cl.6 .............................. A61C 9/00; A61C 8/00
[52] U.S. Cl. ........................... 433/214; 433/172; 433/173
[58] Field of Search ................................. 433/172, 173, 433/174, 175, 176, 201.1, 214

[56] References Cited

U.S. PATENT DOCUMENTS

| | | | |
|---|---|---|---|
| 4,856,994 | 8/1989 | Lazzara et al. | 433/173 |
| 5,108,288 | 4/1992 | Perry | 433/174 |
| 5,338,196 | 8/1994 | Beaty et al. | 433/172 |
| 5,431,567 | 7/1995 | Daftary | 433/172 |
| 5,492,471 | 2/1996 | Singer | 433/173 |

OTHER PUBLICATIONS

The Emergence Profile System; 8 Pg. booklet from 3i.
Emergence Profile Prosthetics; 8 Pg. booklet from 3i.
Wide Diameter Prosthetics; 12 Pg. booklet from 3i.
Bio–Esthetic Technique Man.; 6 p.trifold bk Steri–Oss.
Bulletin #IISO48 Rev A. Sep. 1995; 3i.
Bulletin #IISO29 Rev B. Sep. 1995; 3i.
Abutment Option Height Req.

*Primary Examiner*—Cary E. O'Connor
*Attorney, Agent, or Firm*—Curtis L. Harrington

[57] ABSTRACT

A complete dental implant system and method uses a standard shape if both the healing abutment, the impression coping and in the final tooth prosthesis. A series of four to five standard shapes which will oppose the gum tissue will be used for different types of teeth, and to enable control over the size and shape of material will be introduced into the patient's tissue, for a single tooth replacement beginning at the time the gums above the threaded bone penetrating implant are opened and the healing around the pre-specified shape is started. This causes the supporting adjacent tissues to have to heal but once. The impression coping and healing abutment which have the same shape facilitate the non-damaging insertion and removal from the gum area and eliminate the need for extensive work on the implant tooth prosthesis while it is within the patient's oral cavity. The system enables less work to be done on the prosthesis while the patient is in the chair, and thus more control at the dental lab. Three alternatives are disclosed for forming the final tooth prosthesis, including (1) formation of the prosthesis over coping having a shape specified collar, (2) beginning with a titanium blank, and (3) beginning with a titanium rough preparation.

25 Claims, 10 Drawing Sheets

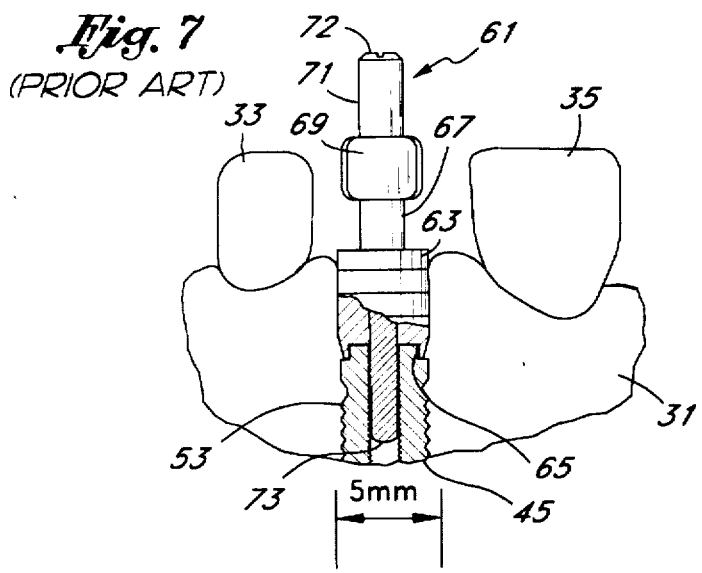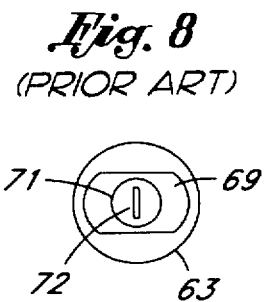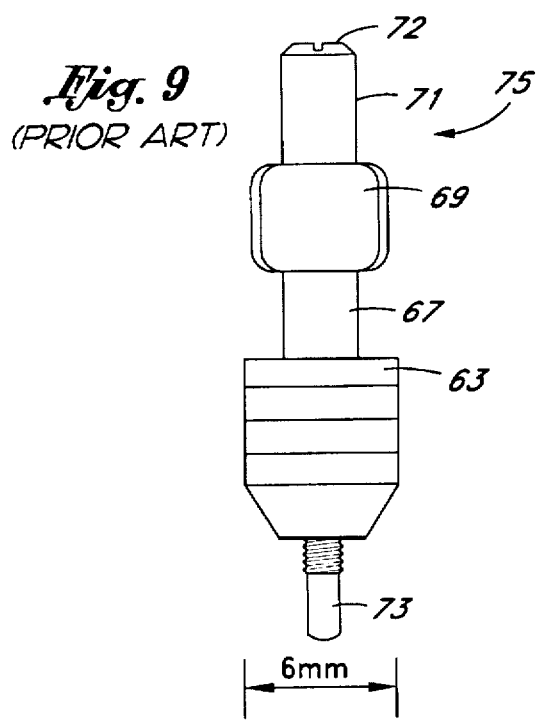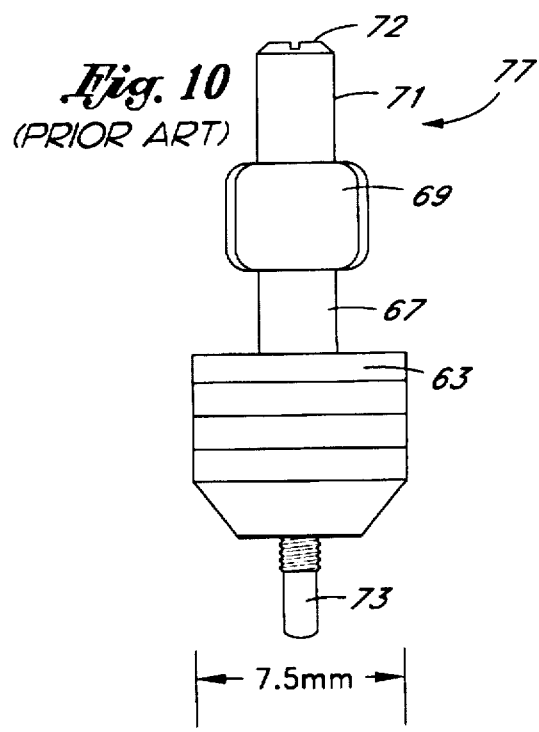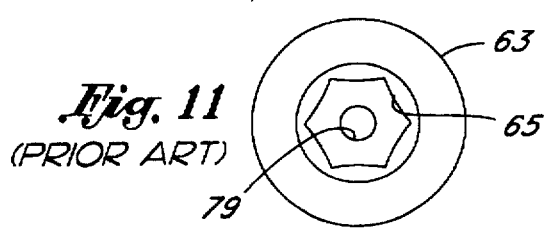

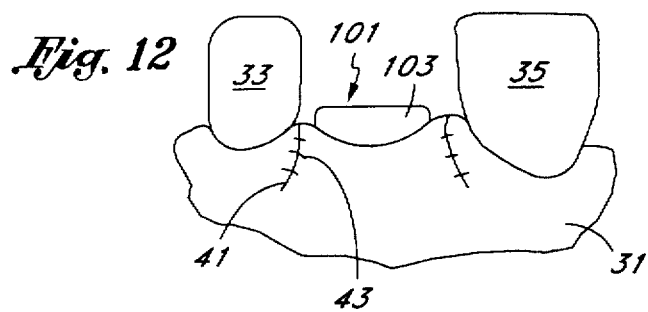
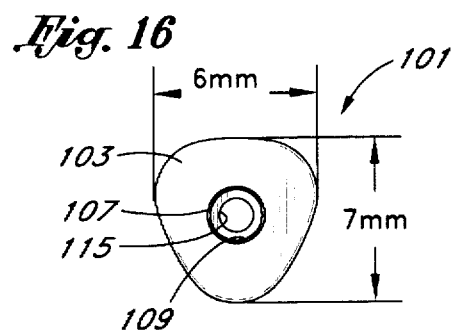
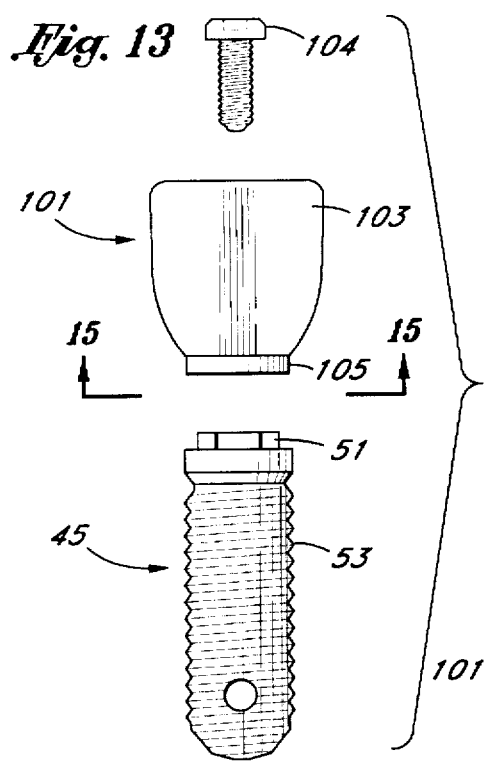
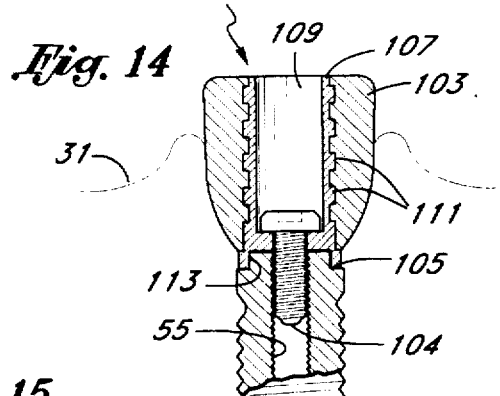
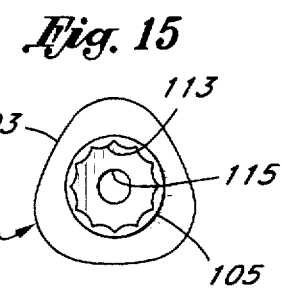
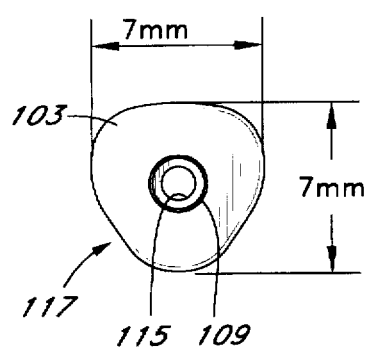
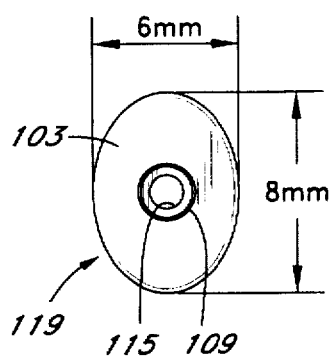
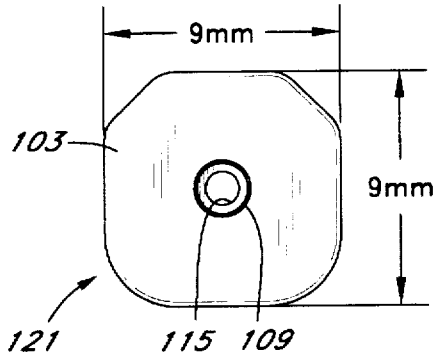

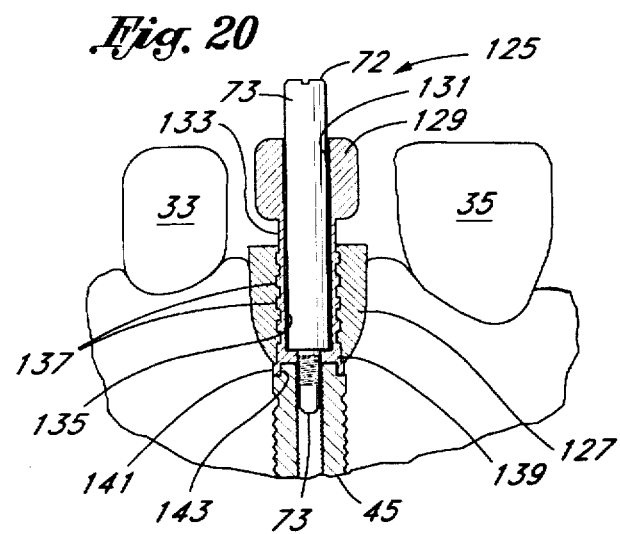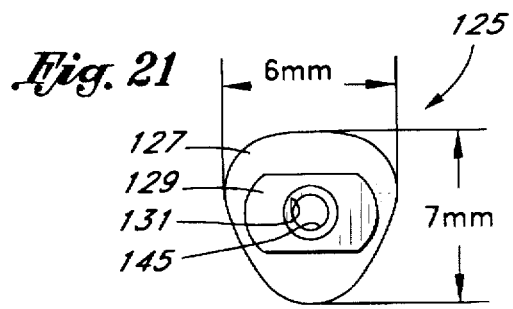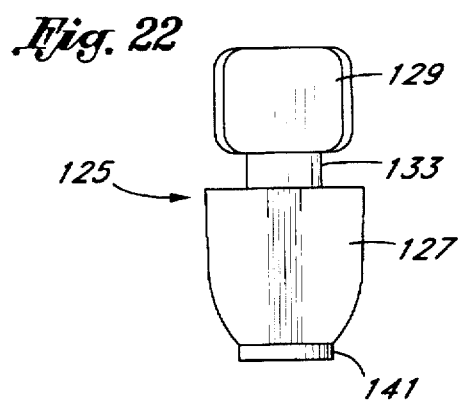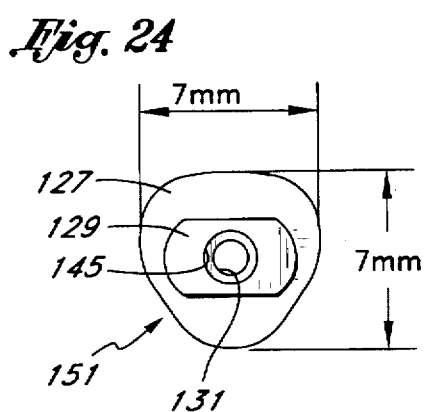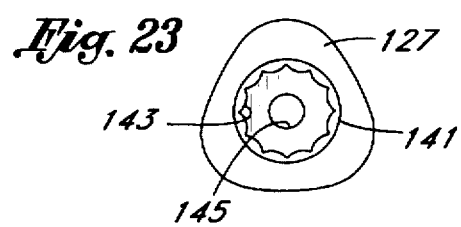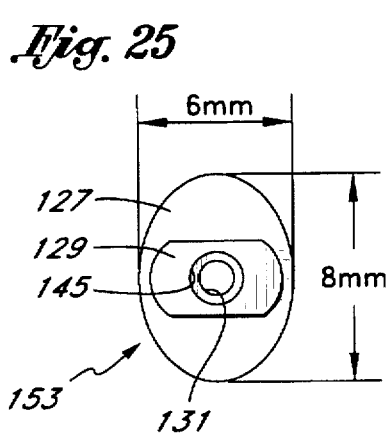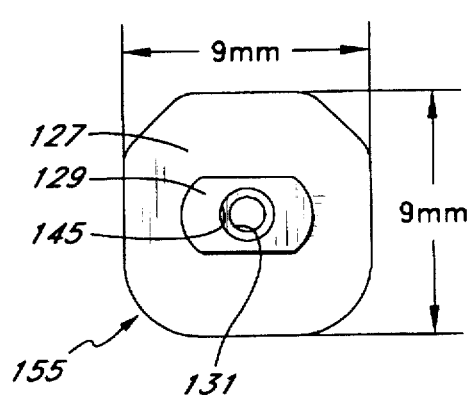

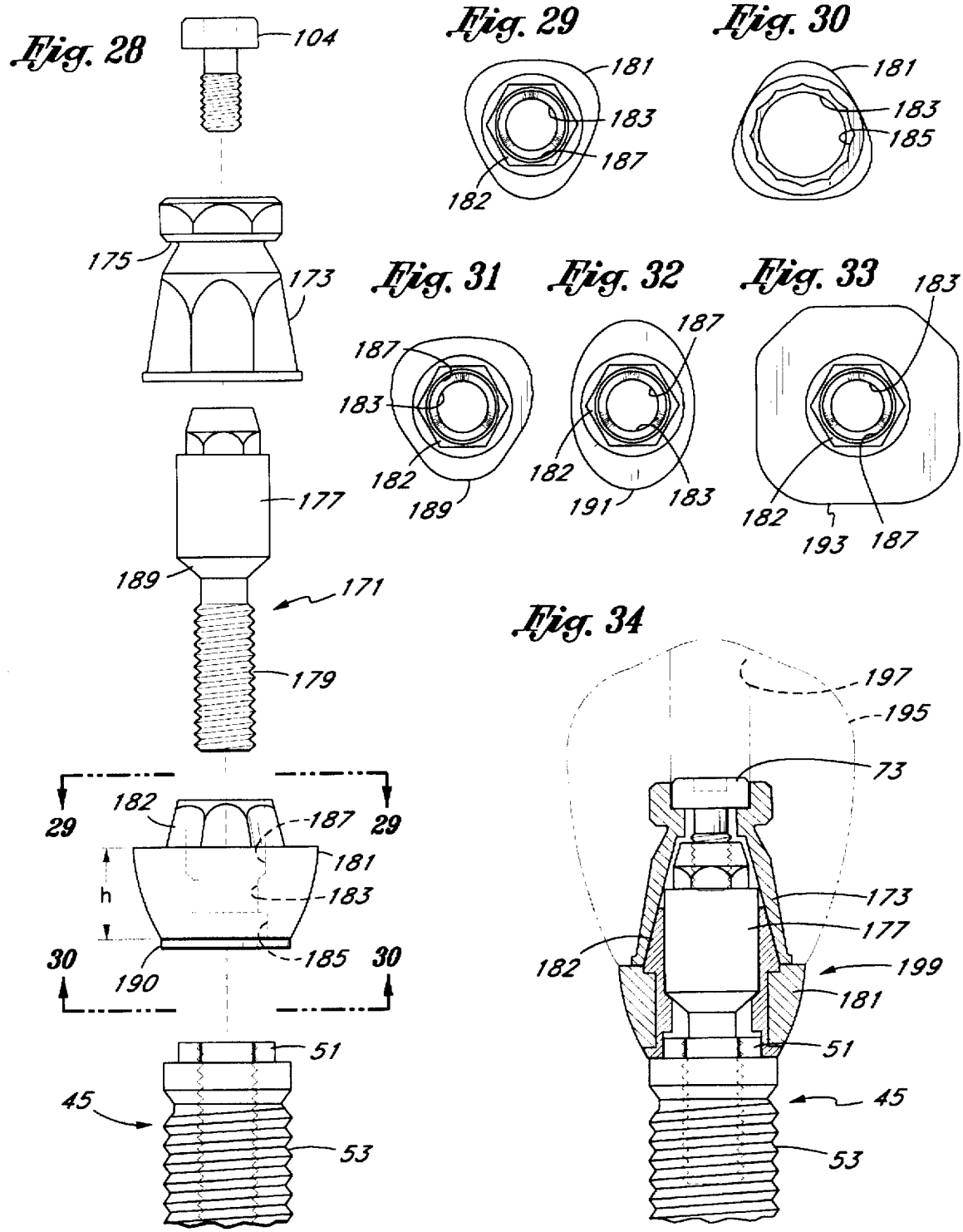

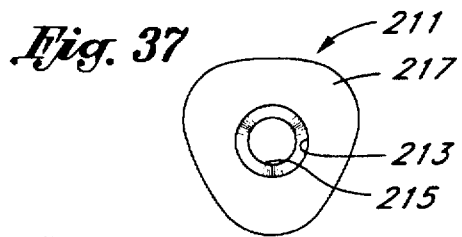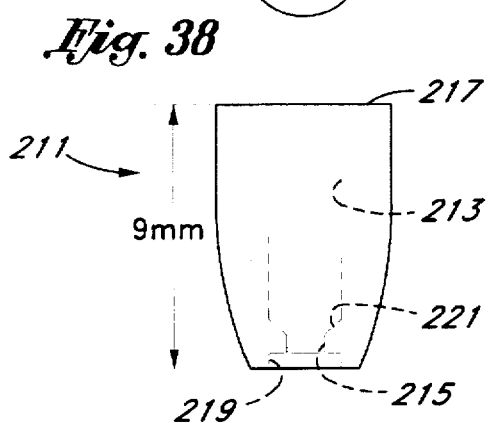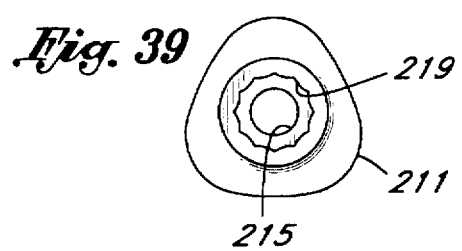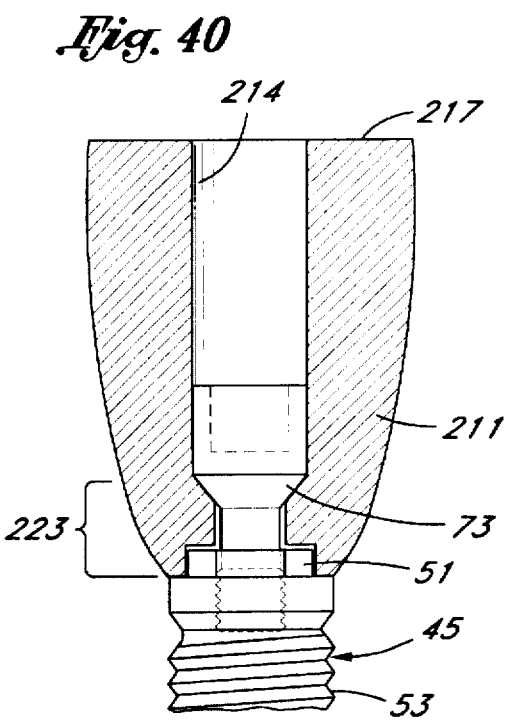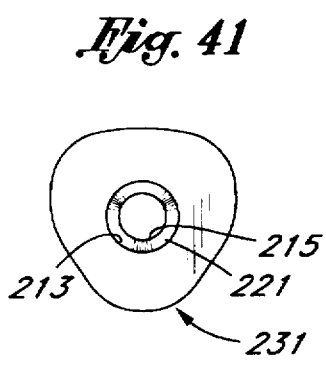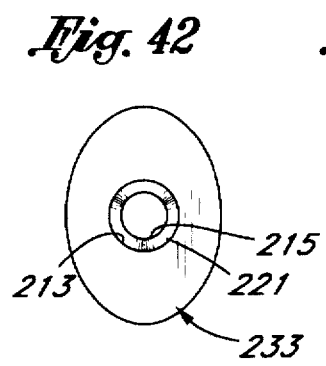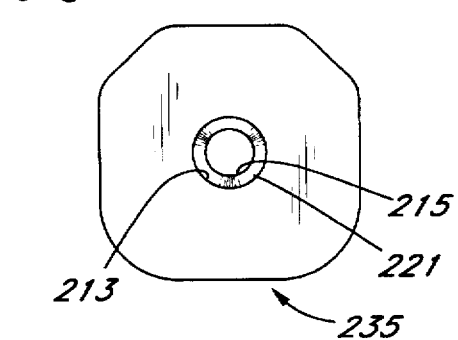

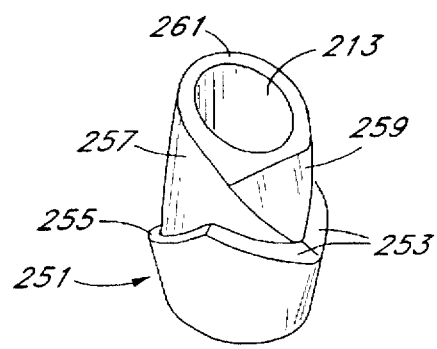
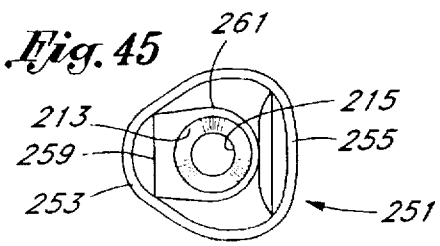
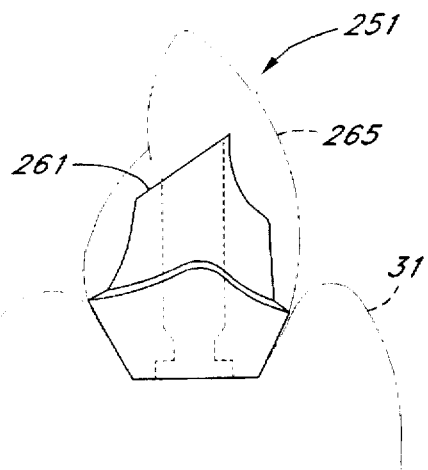
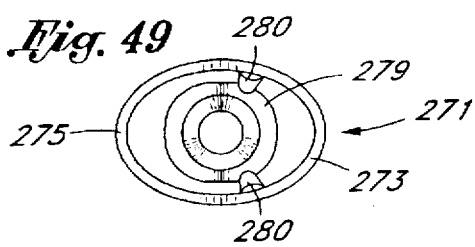
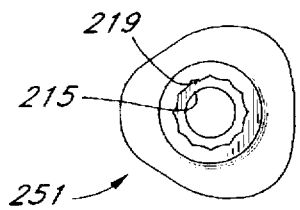
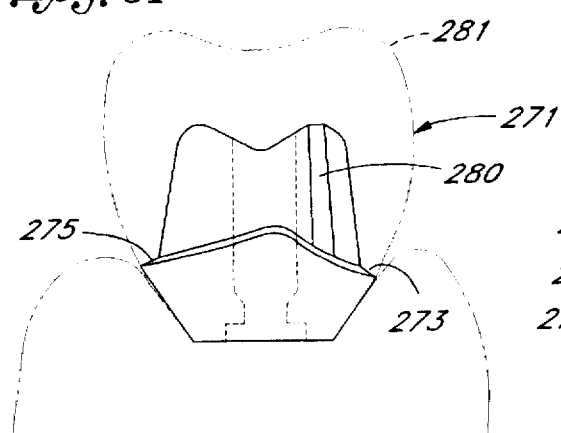
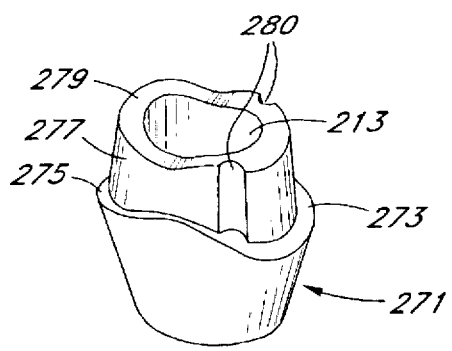
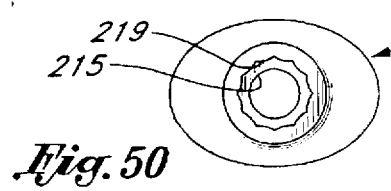

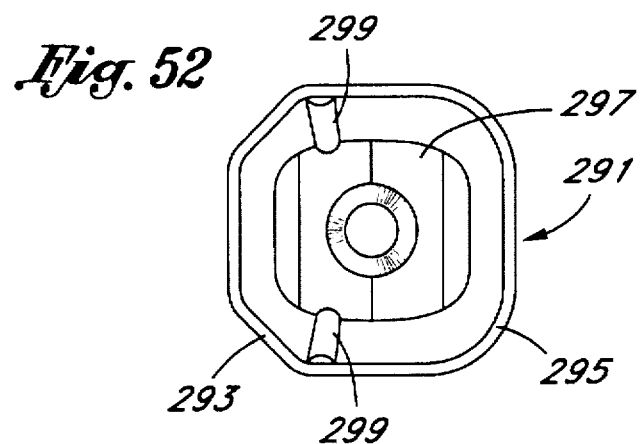
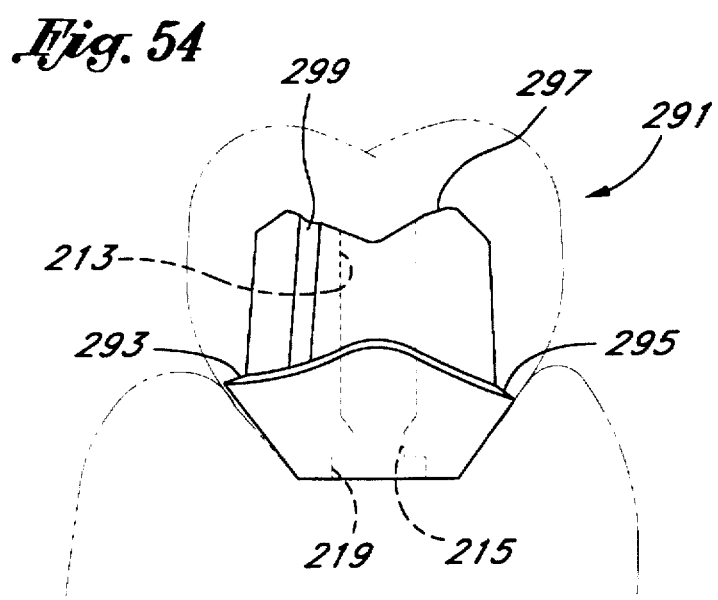
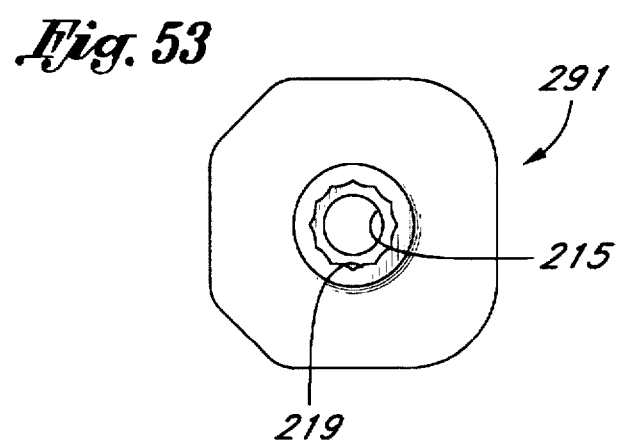

5,759,036

COMPLETE DENTAL IMPLANT SYSTEM AND METHOD

FIELD OF THE INVENTION

The present invention relates to the field of dental implants and physical implements for facilitating the use of the dental implant system, and especially a system which enables a defined form to be used to help shape the patient's gum tissue to promote proper healing esthetics and to reduce tissue trauma during the several steps required to complete the implant process.

BACKGROUND OF THE INVENTION

Two main systems are in wide use today and which permit dentists to perform implant procedures. These systems are the cementable system which uses a platform secured by the bone implant upon which the replacement tooth is cemented, and the screw-retained system which utilizes a round abutment followed by a threaded tooth structure. Both of these systems have significant shortcomings, as will be discussed.

The cementable-only system uses a threaded or cylinder, bone penetrating implant which is surgically tapped or threadably "turned" or screwed into bone tissue, after the root and otherwise old tooth material has since been removed. The steps leading up to the bone implant are similar for both the cement-only, screw-retained systems, as well as for the inventive system to be explained in the summary.

The cement-only system involves the placement of a metal abutment platform held in place by threaded attachment to the bone implant. This metal abutment platform is not removed during further treatment of the patient. If the need arises to change the shape of this metal abutment, it is shaped while in the patient's mouth. The dental drill can generate significant heat in grinding down the abutment platform which is transmitted directly to the patient's surrounding tissues.

The metal abutment members are available in a variety of shapes, but the size along the main axis is generally similar. However, the depth of gum into which each abutment platform is placed varies by patient. It is generally not known to what extent the abutment platform will extend above the gum line. Where the abutment platform extends significantly above the gum, or otherwise interferes with surrounding dental structures, it must be significantly ground.

Once the abutment is in place it is not removed. The resulting replacement tooth is formed, typically at a dental lab, using traditional crown & bridge clinical and laboratory procedures. A new tooth is therefore formed by taking an impression of the abutment post & platform and by sculpting the tooth based upon its type and any dimensions supplied by the dentist. Since the general shape and size of the platform is known, the end of the tooth prosthesis to be cemented to the abutment platform will have a shape and contour generally accommodating the abutment platform. During the fitting and cementing of the tooth prosthesis onto the abutment platform, the traditional dental techniques are used.

Since the threaded member holding the metal abutment platform is completely embraced by a solid tooth prosthesis, the abutment platform cannot be re-accessed without physically breaking off the tooth prosthesis from the abutment platform. As a result, any further adjustments which need be made to the implant such as tightening or replacement can only be made by breaking off the tooth prosthesis and removing the abutment platform.

Since the abutment platform is designed to be permanently installed, all of the subsequent work in fitting, shaping and forming the tooth must be done in the mouth. This can result in more chair time since the tooth prosthesis will need to be worked while it is in place.

In formation of the tooth prosthesis, the dental lab has to accept the front edge of the platform supplied by the impression which will fit adjacent and over the abutment platform, to extend downwardly. If the edge or platform off by just a bit, the metal from the abutment platform will show. The metal from the abutment platform, even if it does not show, will have a chance for later exposure if it does not extend downwardly far enough over the abutment platform, and the gums recede somewhat in future.

In general, and this encompasses a wide variety of aspects of physical workability in the dental lab, there is poor aesthetic control of the resulting tooth prosthesis. Much of the labor is spent continually forming a lower surface which will fit the abutment platform which has been altered by the dentist. In effect, each lower surface has to be custom made. This labor effort is multiplied each time a tooth in the cementable system is made. The abutment platform cannot be removed and sent to the lab since the adjacent tissues would collapse and would perhaps become damaged without the support of the abutment platform. This is one of major reasons why the abutment platform is kept permanently in place.

In the screw retained system, once the bone penetrating implant is in place, the gum tissue is folded over and sealed for a period of 4–6 months. Once the penetrating implant has been exposed to the patient's system for a sufficiently long period of time, the gums are again opened and a circular healing abutment is fitted into the hole previously occupied by the missing tooth by threaded engagement with the implant. The gum tissue surrounding the healing abutment are sutured and the gums tissue around the healing abutment left to heal for a period of six to eight weeks.

Even though dental implants use a screw turnable within a tooth prosthesis, currently available healing abutments are limited to a simple tablet shaped or cylindrically shaped form which threadably turns into the implant and forces its way into the gum tissues. Although the radial symmetry allows the healing abutment to simply screw in, the surrounding tissues are made to begin to heal in a circular configuration.

After the tissues heal, a tooth prosthesis is again forced into the space occupied by the round healing abutment, but the tooth prosthesis will have a cross sectional area which is not round and which may be larger than the space occupied by the healing abutment. As a result, the tissues are again damaged and must again reheal. This can result in additional scarring from having experienced an additional trauma, and tissue instability which would cause the tissue to change or recede. In addition, the unstable, unpredictable tissue will take longer to heal.

Other steps in the current screw retained system involve the use of an impression coping which is another similar, round member which is placed in the patient's threaded or cylinder, but generally bone penetrating implant and which has a relatively elongate channel to protect the screw used to hold it in place. The impression is then taken around the impression coping, and the impression coping is removed and again the round healing abutment is replaced.

The laboratory uses the resulting impression to form a prosthetic tooth, generally from a white tooth colored porcelain material baked over a metal material common in dental applications. The prosthetic tooth is formed on a second structure which may be referred to as a prosthetic support abutment which is also round. This structure is either made or purchased by the dental laboratory based upon the stone poured impression taken with the impression coping. In the stone formed impression of the patient's mouth, the round prosthetic support abutment is put in place and the prosthetic tooth is built on top of it. Again, the prosthetic tooth or crown must be fabricated to fit unnatural round tissue. The result is unstable tissue & compromised esthetics.

The standard screw-retained process has the advantage that the prosthetic tooth can be better worked out of the patient's mouth and can also be worked upon with its threaded retention environment. This enables the dental lab to have better control over the result. However, the resulting prosthetic tooth will still have a significant variance in the final product since both the healing abutment and impression coping are round which still causes the dental lab to form the prosthetic tooth in a conventional fashion, to fit a round tissue shape.

Further, the resulting prosthetic tooth has a lower area which transitions from a round base cap intended to mate with a hexagonal structure protruding slightly from the top of the bone penetrating implant. As a result, the tissue immediately adjacent the round base cap has not only less support than the tissue which lies next to the point of emergence of the prosthetic tooth, but virtually no support. This, combined with the effect by employing a round healing abutment and then with a round but sharply conically extending prosthetic tooth volume acts to again cause trauma to the surrounding tissue.

Although it would be helpful in terms of overall prosthetic quality to maximize the area of tooth-colored porcelain material to extend as low as possible on the prosthesis, it is more important to lend support to the surrounding tissues and to control the overall quality of the prosthesis. Consistency between the healing abutment, impression coping, and final tooth prosthesis is desired, but absent in both the screw retained and cementable systems. Further, if the tooth prosthesis is damaged, and although it has the ability to be removed and sent to the dental lab for repair, the only available structure for the patient as a replacement during repair is the healing abutment, which will not match the tissue space and will leave open tissues during the time of repair, in the case of a screw retained system. The cemented system will not leave the patient's tissues exposed since the abutment platform must stay in place, but removal of the tooth prosthesis could damage it further. If damaged enough, it will have to be re-constituted with an amount of effort and cost equivalent to its original formation, accompanied by a fresh impression.

What is therefore needed is a system which will, after insertion of the bone penetrating implant member, enable adequate lateral tissue support. The needed system will enable the tissues to heal only a single time to reduce scarring and promote a stronger formation in a configuration which will match the final geometry of the final implant. The needed system should provide better control of aesthetics and greater surface area of tooth colored material. The needed system should also facilitate easy removal of the tooth prosthesis and replacement by a structure to protect the gum tissue while the tooth prosthesis is being repaired.

SUMMARY OF THE INVENTION

The complete dental implant system and method of the present invention is one which will use a standard root form shape in both the healing abutment, the impression coping and in the final tooth prosthesis. A series of four to five standard root form shapes which will oppose the gum tissue will be used for different types of teeth. However, the same size and shape of material will be introduced into the patient's tissue, for a tooth replacement once the gums above the threaded bone penetrating implant are opened and the healing around the shape is begun. The healing abutment will have an exacting lower shape for supporting adjacent tissues and to enable the surrounding tissues to have to heal but once.

At the time of impression, the healing abutment is removed and immediately replaced with an impression coping having the same root form shape and size as the healing abutment with regard to the areas opposing the gum tissue. Once the impression is taken, the healing abutment is again re-inserted, the patient to await the formation and return of the prosthetic tooth from the dental lab. At the dental lab, the impression coping which is used to create the stone model has the exact shape which is carried by the healing abutment, and enables consistency of the gum opposing portion of the tooth shape to be maintained. Further, the system enables less work to be done on the prosthesis while the patient is in the chair, and thus more control at the dental lab. The result is better tissue stability, better esthetics and reduced chair tim for the dental clinician.

The invention facilitates the guiding of soft tissue healing to ideal anatomical contours. The structures of the invention are easy to modify, either to add shapes or to contour. The four central shapes, centeral, lateral, bisuspid and molar keep the number of standard sizes to the minimum practical number.

BRIEF DESCRIPTION OF THE DRAWINGS

The invention, its configuration, construction, and operation will be best further described in the following detailed description, taken in conjunction with the accompanying drawings in which:

FIG. 7 is a view of a section of gum tissue including a space where a tooth implant is in plac and illustrating an impression coping having a prior art circular lower surface;

FIG. 8 is a top view of the prior art impression coping shown in FIG. 7;

FIG. 9 is a view of the prior art impression coping similar to but larger than the impression coping of FIG. 7 for larger sized teeth;

FIG. 10 is the largest size prior art impression coping and having a lower diameter of seven and a half millimeters;

FIG. 11 is a bottom view of the impression coping of FIG. 7 and illustrating the hexagonal depression which provides orientational keying for the impression to be taken;

FIG. 12 is a view of a section of gum tissue including a space where a bone penetrating implant is in place and illustrating a healing abutment in accord with the present invention;

FIG. 13 is an exploded view of the healing abutment of FIG. 12 and including the bone implant which supports the healing abutment and threaded screw used to secure the healing abutment;

FIG. 14 illustrates a sectional view of the healing abutment shown in place with respect to the bone implant in an orientation similar to that shown in FIG. 13;

FIG. 15 illustrates a bottom view of the healing abutment of the present invention and illustrating the overall shape and a twelve position depression to permit more finely selective orientation with respect to the bone implant;

FIG. 16 is a top view of the healing abutment of the present invention and illustrating the overall dimensions of a six millimeter by seven millimeter rounded corner triangular shape;

FIG. 17 is a top view of a second, different sized healing abutment of the present invention and illustrating the overall dimensions of a seven millimeter by seven millimeter rounded corner triangular shape;

FIG. 18 is a top view of a third, different sized healing abutment of the present invention and illustrating the overall dimensions of a six millimeter by eight millimeter rounded oval shape;

FIG. 19 is a top view of a fourth, different sized healing abutment of the present invention and illustrating the overall dimensions of a nine millimeter by nine millimeter square shape having a pair of angled corners;

FIG. 20 is a view of a section of gum tissue including a space where a tooth implant is in place and illustrating an impression coping in accord with the present invention;

FIG. 21 is a top view of the inventive impression coping shown in FIG. 20 and illustrating the overall dimensions of a six millimeter by seven millimeter rounded corner triangular shape;

FIG. 22 is a plan view of the impression coping of FIG. 20 and illustrating the external features thereof;

FIG. 23 is a bottom view of the impression coping of FIGS. 20-22 and illustrating the twelve position depression to permit optimum positioning;

FIG. 24 is a top view of a second, different sized impression coping of the present invention and illustrating the overall dimensions of a seven millimeter by seven millimeter rounded corner triangular shape;

FIG. 25 is a top view of a third, different sized impression coping of the present invention and illustrating the overall dimensions of a six millimeter by eight millimeter rounded corner oval shape;

FIG. 26 is a top view of a fourth, different sized impression coping of the present invention and illustrating the overall dimensions of a nine millimeter by nine millimeter square shape having a pair of sharply angled corners;

FIG. 28 is an exploded view of a tiered prosthetic tooth support having interchangeable collars corresponding to similarly located shapes on the healing abutments and impression copings of FIGS. 12-27;

FIG. 29 is a top view of the interchangeable collar shown in FIG. 28 and having a dimension overall dimensions of a six millimeter by seven millimeter rounded corner triangular shape;

FIG. 30 is a bottom view of the interchangeable collar shown in FIGS. 28 & 29;

FIG. 31 is a top view of a second interchangeable collar having the overall dimensions of a seven millimeter by seven millimeter rounded corner triangular shape;

FIG. 32 is a top view of a third interchangeable collar having the overall dimensions of a six millimeter by eight millimeter rounded oval shape;

FIG. 33 is a top view of a third interchangeable collar having the overall dimension of a nine millimeter by nine millimeter square shape with a pair of angled corners;

FIG. 34 is a sectional view of the assembled tiered prosthetic tooth support of FIG. 28 and shown with the baked porcelain tooth prosthesis shown in phantom;

FIG. 37 is a top view of a solid metal blank from which a tooth prosthesis can be carved and constructed as a single support body, and having overall dimensions of a six millimeter by seven millimeter rounded corner triangular shape.

FIG. 38 is a plan view of the solid metal blank of FIG. 37 and illustrating the internal structures in dashed line format;

FIG. 39 is a bottom view of a solid metal blank shown in FIGS. 37-38;

FIG. 40 is a sectional view of the solid metal blank shown in FIGS. 37-39 shown in position over the bone penetrating implant, but without having been sculpted to its final form;

FIG. 41 is a top view of a second solid metal blank but having overall dimensions of a seven millimeter by seven millimeter rounded corner triangular shape;

FIG. 42 is a top view of a third solid metal blank but having overall dimensions of a six millimeter by eight millimeter rounded corner oval shape;

FIG. 43 is a top view of a fourth solid metal blank but having overall dimensions of a nine millimeter by nine millimeter square shape with two of the corners having angled corners;

FIG. 44 is a perspective view of a rough preparation having internals in accord with FIGS. 37-43, but having an external shape in rough preparation for supporting a tooth prosthesis and shaped as an anterior tooth;

FIG. 45 is a top view of the rough preparation shown in FIG. 44;

FIG. 46 is a bottom view of the rough preparation shown in FIGS. 44 & 45;

FIG. 47 is a side view of the rough preparation of FIGS. 44-46 shown in place adjacent schematically illustrated gum tissue, and shown supporting a porcelain tooth prosthesis shown in phantom;

FIG. 48 is a perspective view of a rough preparation having internals in accord with FIGS. 37-43, but having an external shape in rough preparation for supporting a tooth prosthesis and shaped as a posterior/bicuspid tooth;

FIG. 49 is a top view of the rough preparation shown in FIG. 48;

FIG. 50 is a bottom view of the rough preparation shown in FIGS. 48 & 49;

FIG. 51 is a side view of the rough preparation of FIGS. 48–50 shown in place adjacent schematically illustrated gum tissue, and shown supporting a porcelain tooth prosthesis shown in phantom;

FIG. 52 is a top view of a rough preparation having internals in accord with FIGS. 37–43, but having an external shape in rough preparation for supporting a tooth prosthesis and shaped as a molar tooth;

FIG. 53 is a bottom view of the rough preparation shown in FIG. 52; and

FIG. 54 is a side view of the rough preparation of FIGS. 52 & 53 shown in place adjacent schematically illustrated gum tissue, and shown supporting a porcelain tooth prosthesis shown in phantom.

DETAILED DESCRIPTION OF THE PREFERRED EMBODIMENT

Figure 1:
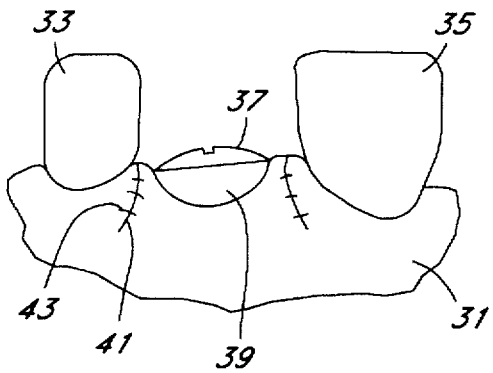
FIG. 1 is a view of a section of gum tissue including a space where a tooth implant is in place and illustrating a healing abutment in accord with the prior art.

The description and operation of the invention will be best described with reference to FIG. 1. A section of human oral gum tissue 31 is shown over a length of the space which would be occupied by three teeth. Implant structures are shown between a first tooth 33 and a second tooth 35. Although several implants may be located next to each other, a single implant located between two natural teeth 33 and 35 represents the most challenging restrictions to working space and proper orientation of the implant.

At the base of the space between the teeth 33 and 35 is shown a cylindrical healing abutment 37 having a straight cylindrical surface 39. As can be seen, the gum tissue 31 may in some circumstances require incision 41 and perhaps some suturing 43. Referring to FIG. 2, the healing abutment 37 is shown in position over a bone implant 45, which is not seen in FIG. 1, being located beneath the gum tissue 31. The healing abutment 37 is threadably turned into threaded engagement with the bone penetrating implant 45 to support the gum tissue 31 surrounding the upper space over the bone implant 45.

The bone penetrating implant 45 is available in a variety of external sizes. Bone penetrating implants for lateral, central and bicuspid teeth are usually 3.75 millimeters, 4.0 millimeters and 5.0 millimeters in diameter. For molars, the 6.0 millimeter diameter implant is generally exclusively used. In the description which follows, the proper sized bone penetrating implant 45 is assumed to be used and its particular dimensions will not be further discussed.

In FIG. 2, other portions of the cylindrical healing abutment 37 can be seen, including an upper slot 47 to assist turning the healing abutment 37 into place, and a threaded extension 49 which extends downwardly from the healing abutment 37. As can be seen, the threaded extension 49 is preferably formed integrally with the healing abutment 37 since healing abutment 37 is completely cylindrical and can turn without interfering with the first and second tooth 33 and 35.

The upper end of the bone penetrating implant 45 has an extremely shallow hexagonal projection 51 used for rotationally positioning a prosthetic restoration which will be shown later. There is no matching hexagonal space on the underside of the healing abutment 37, since the healing abutment 37 must be free to be threadably rotated into place. Also seen is an externally threaded surface 53 of the bone implant 45. This thread is used to turnably bore the bone implant 45 into the bone tissue adjacent the space previously occupied by the diseased tooth removed to make room for the implant.

Figure 3:
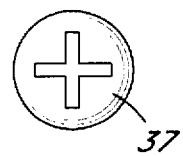
FIG. 3 is a top view of the prior art healing abutment shown in FIG. 1.
Figure 4:
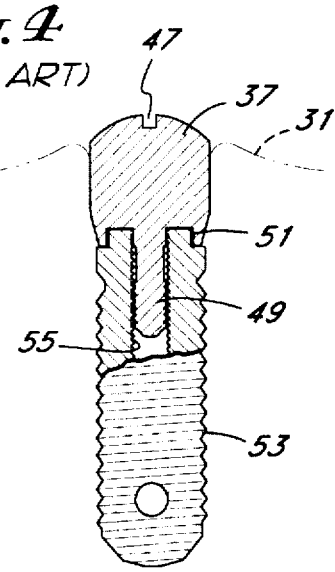
FIG. 4 is a sectional view of the healing abutment shown in place with respect to the bone implant in an orientation similar to that shown in FIG. 2.

Referring to FIG. 3, a top view of the cylindrical healing abutment 37 is shown. In FIG. 4, a sectional view shows an internally threaded surface 55 of the bone implant 45 which engages the threaded member 49.

Figure 5:
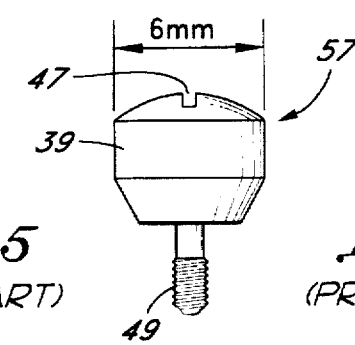
FIG. 5 illustrates a differently sized prior art healing abutment at six millimeters in diameter.
Figure 6:
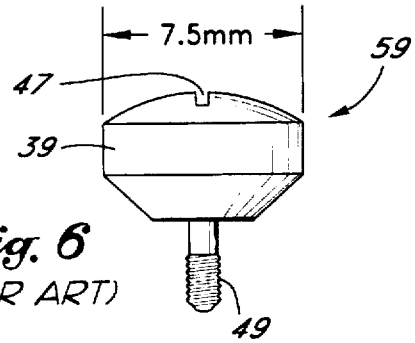
FIG. 6 illustrates a differently sized prior art healing abutment at seven and a half millimeters in diameter.

The bone implant 45 will generally be of the same diameter regardless of the tooth prosthesis it will support, but perhaps with some variation between molars and the smaller teeth. However, since the space previously occupied by the removed tooth will differ, a series of different sized cylindrical healing abutments will be used. The healing abutment 37 of FIG. 1 is shown to be five millimeters in diameter. Referring to FIG. 5, a healing abutment 57 having a diameter of six millimeters is shown, and is used for the next largest size aperture of the teeth. Referring to FIG. 6, a healing abutment having a diameter of seven and a half millimeters is shown for the largest sized apertures. Other structures of the healing abutments 57 and 59 shown in FIGS. 5 and 6 are the same as were shown for healing abutment 37.

Since the screw retained system of FIGS. 1–6 is a cylindrical system, and since the tooth which the implant system is intended to replace has a particular non-cylindrical shape, the tissues are left to partially collapse and begin to heal around a cylindrical object. Allowing the gum tissue 31 surrounding the missing tooth to heal in an unsupported manner will cause damage enough, however, the later placement of the tooth prosthesis which transitions from a round structure to a defined tooth structure will cause further damage to the gum tissue 31. In essence, the gum tissue is left to heal in a first unsupported position, and then it is compressed and jammed back at the time of introduction of the tooth prosthesis.

In the implant preparation process, and after six to eight weeks after the bone implant 45 is affixed to the patient's dental bone structure the gum tissue 31 has healed sufficiently to take a proper impression which will assist the formation of the tooth prosthesis. The impression is taken with the assistance of an impression coping.

Referring to FIG. 7, the bone implant 37's threaded interior is used to facilitate the threaded support of an impression coping 61. The impression coping 61 provides structure which will attach to the impression material and will be removed with the impression material in order to transfer the characteristics of the surrounding gum tissue 31 and the orientation of the bone implant 45. The impression coping 61 has a cylindrical lower section 63 having a shallow hexagonal impression 65 to fit over the shallow hexagonal projection 51 of the bone implant 45. The upper portion of the impression coping 61 has an extension portion 67, a square or rectangular boss 69 and a screw extension tube 71 sitting above the rectangular boss 69. At the top of the extension tube, a head 72 of an elongate threaded screw 73. The use of a special elongate threaded screw 73 enables the dental practitioner avoid having to insert a long screwdriver device into the extension tube 71 and also helps to lessen the possibility of a threaded device falling out of the extension tube 71.

Figure 2:
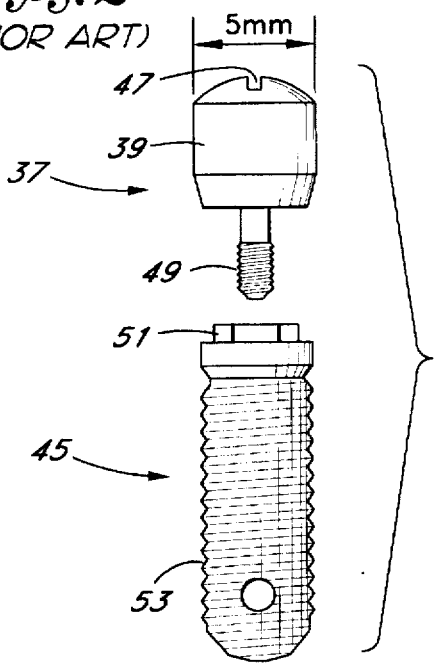
FIG. 2 is an exploded view of the healing abutment of FIG. 1 and including the bone implant which supports the healing abutment and which will support the tooth prosthesis.

The square boss 69 insures that there will be proper orientation when an impression material is introduced simultaneously over the impression coping 61, first and second teeth 33 and 35, and over the section of human oral gum tissue 31 in the immediate vicinity of the area shown in FIG. 1.

Once the impression material covers the impression coping 61 and the rectangular boss 69, the rectangular boss 69 will "key" the position of the extremely shallow hexagonal projection 51 with respect to the impression material. The screw extension tube 71 insures that the upper portion of the impression coping 61 will be taller than the impression material so that the center of the impression coping can be accessed to remove a threaded screw 73 which is shown engaging the significantly smaller threaded internal diameter within the bone penetrating implant 45 to hold the impression coping 61 in place with respect to the bone implant 45.

When the impression is taken, and the threaded screw 73 is removed, the impression coping 61 is removed with the impression material. With the impression coping 61 removed, a positive mold of the section of human oral gum tissue 31, first tooth 33, and a second tooth 35 will also carry an impression of the impression coping 45 and its orientation with respect to the extremely shallow hexagonal projection 51. If the positive mold is made with a negatively threaded support, the positive mold can also include the position and orientation of the bone implant 45. Then, the dental lab technician can add a prosthesis support which is also amenable to threaded connection to the bone implant 45. The lab technician then begins shaping a tooth prosthesis to fit over the prosthesis support.

In forming the tooth prosthesis, the center of the tooth prosthesis is left open so that the tooth prosthesis and tooth prosthesis support can be threadably secured onto the bone implant 45 when the tooth prosthesis is placed in the patient's mouth. Referring to FIG. 8, a top view of the impression coping 61 illustrates the head 72 of the screw 73 within the screw extension tube 71. Other details shown are the circular profile of the impression coping 61, in particular the cylindrical lower portion 63. The diameter of the round cylindrical portion 63 is the same as the straight cylindrical surface 39 of the cylindrical healing abutment 37.

Referring to FIG. 9, a series of differently sized impression copings will also be used, each of which match the round diameters of the healing abutments 37, 57, and 59. The impression coping 61 of FIG. 7 is shown to be five millimeters in diameter. Referring to FIG. 9, an impression coping 75 having a diameter of six millimeters is shown, and is used for the next largest size aperture of the tooth being replaced. Referring to FIG. 10, an impression coping 77 having a diameter of seven and a half millimeters is shown, and is used for the largest size aperture. In FIG. 11, the shallow hexagonal depression 65 is explicitly shown. Also seen is a bore 79 through the impression coping 61 through which the threaded screw 73 extends to secure the impression coping 61.

When the final tooth prosthesis is formed, it will be forced into a round space in the section of human oral gum tissue 31 with a widely flaring prosthetic tooth material which will re-injure the gum tissue 31. Not only have the round cylindrical surfaces 39 and 63 allowed the gum tissue 31 to begin to heal in a generally unsupported manner, it has also forced the gum tissue 31 to heal a round shape which will be different from the shape of the formed tooth prosthesis.

Referring to FIG. 12, a section of human oral gum tissue 31 is again shown over a length of the space which would be occupied by three teeth. An inventive healing abutment 101 is shown between first tooth 33 and second tooth 35. Of the healing abutment 101, only the upper composite material 103 is seen in FIG. 12. The composite material is preferably a composite like resin which is generally described in dentistry as a composite resin that is either light (photo) cured or chemical cured, and may be tooth colored. This material is manufactured in many different ways both within and outside of the dental field and is sold under a variety of product names. It is impossible to list every such product on the market, and as such, a more detailed description is un-necessary. Any material which is easily adjustable, bondable to or capable of being added to, other composite-like resin materials, plastic materials, acrylic materials, whether firm or hard are included. Other variations on this material include may include highly polish able materials, including tooth colored materials, as well as any material compatible for use in the oral cavity and which possesses the above listed characteristics.

For example, one such material is commercially available under the trademark name HERCULITE, by the Dentsply Company.

More importantly, and as can be seen from FIG. 12, the shape of the healing abutment 101 has a shape as it rises above the gums as an emerging shape which matches the shape of the previous tooth. In particular it carries its proper shape and even from the side view of FIG. 12 it is readily seen that the emerging shape represents a properly sized progression in size from tooth 33 to the healing abutment 101 and then to tooth 35. In effect, the shape of the healing abutment 101, although not exactly matched to the exact dimensions of the patient's tooth which has been removed, has a general shape corresponding to the shape of the tooth which has been removed. In effect, the gum tissues 31 are allowed to heal while supported in their natural shape, and against a form which corresponds to the form of the tooth which has been lost.

Referring to FIG. 13, an exploded view of the assembly which for FIG. 1 was shown partially above and partially below the gum tissue 31 is shown. A threaded, preferably gold, screw 104 is used for securing the healing abutment 103 to the bone penetrating implant 45. The healing abutment 101 is shown as having a lower metal rim 105 below the upper composite material 103. All of the metal in the healing abutment 101 is preferably made of titanium. The healing abutment is also located above the upper end of the bone implant 45 and its extremely shallow hexagonal projection 51. Since the shape of the composite material is not circular and is specific to the type of tooth removed, it will also need to be rotationally keyed, and it will also use the projection 51.

Referring to FIG. 14, a sectional view taken through the gum tissue 31 of FIG. 12 illustrates the internal extent of the metal used in the healing abutment 101. The healing abutment 101 includes a metal portion 107 of which the lower rim 105 is a part. The metal portion 107 includes a central bore 109 of sufficient size to accommodate the threaded screw 104 completely therethrough.

The outside of the metal portion 107 carries a series of spaced circular lands 111 for the purpose of even more securably affixing the upper composite material 103 and insuring that it will not be easily removable. Within the lower rim 105, a twelve position depression 113 is carried. The twelve position depression 113 is hexagonally compatible since it could interfit with either a hexagonal shape or a matching twelve position extension. Both a twelve position depression and a hexagonal depression is hexagonally compatible. It is desireable to have more than twelve parts of a 360° circle as detentional rotational choices, but without sacrificing the rotational stability needed by the tooth prosthesis. For example, an eighteen position depression would give three times the detentional choices over a standard hexagon fitting.

The twelve position depression has twice the angles of a hexagonal fitting, and easily fits with the extremely shallow hexagonal projection 51. The twelve position depression 113 is an outwardly directed and mutually inwardly disposed twelve position depression which enables the hexagonal projection 51 to achieve 12 different positions. The twelve position depression 113 is outwardly directed with respect to the healing abutment 103 since it is downwardly directed with respect to the drawing of FIG. 13. The twelve position depression 113 is mutually inwardly disposed because the angled portions of the twelve positions are facing each other.

Instead of only allowing six positions as would a simple hexagon fitting, the twelve position depression 113 enables twelve different positions to be achieved. This enables the dental practitioner to obtain a non-rotational fitting while having a more than necessary number of angular choices in orienting the healing abutment 101 onto the bone implant 45. Also shown is the aperture 115 which is permits the threaded surface of the threaded screw 104 to pass through but does not allow the enlarged screw head to pass through to enable the healing abutment 101 to be held in place.

Referring to FIG. 15, a bottom view of the healing abutment 101 illustrates in greater detail the twelve position depression 113, as well as the overall curved or rounded corner triangular shape of the upper composite material 103. The term rounded corner relates to the transition between the main triangular surface and the adjacent triangular surface, in effect, replacing a sharp corner with a rounded edge.

Referring to FIG. 16, the overall dimensions of the upper composite material 103 portion of the healing abutment indicates that the nominal size may be about seven millimeters at the widest point, and six millimeters at the narrowest point. The minimum and maximum dimensions may vary depending upon the sizes believed to form the best fit to construct the system. The size of the maximum dimension for the healing abutment 101 may vary between about four to about eight millimeters. The size of the minimum dimension for the healing abutment 101 may vary between four to about seven millimeters.

FIG. 16 is the first glimpse of the deviation from a purely cylindrical shape had by the healing abutment 101, and the other components of the inventive implant system. The deviation from the cylindrical shape is hereafter referred to as an acylindrical shape. This includes deviations in a direction perpendicular to any radial line extending from the radial center, since each of the shapes are somewhat tapering.

As will be seen, the aspect ratios in the acylindrical shapes between the widest diameter or width and the narrowest diameter or width will vary. The invention contemplates a ratio of the preferable widest dimension to the narrowest dimension of from about unity to about 1.65. Based upon the greatest magnitude of the maximum dimension given for the range of sizes for the healing abutment 101 and the minimum magnitude of the minimum dimension given for the range of sizes for healing abutment 101, it has a maximum possible ratio of the widest dimension to the narrowest dimension of 2.0.

As will be seen for rectangular shapes some of the rounded corners will be slightly angled, but those aspect ratios of such rounded rectangular shapes will vary much, even if measured from a diagonal. However, where specific and unusual tooth sizes are present, it is contemplated that the aspect ratio could rise to as high as 2.5.

Other healing abutments have different shapes for location at different positions in the oral cavity, depending upon the size of tooth which the tooth implant is to replace. Referring to FIG. 17, the overall dimensions of the upper composite material 103 portion of a healing abutment 117 indicates that one nominal size is seven millimeters at both the widest and narrowest perspectives. The size of the maximum dimension for the healing abutment 117 may vary between about five to about eight millimeters. The size of the minimum dimension for the healing abutment 117 may vary between four to about eight millimeters. The resulting maximum possible ratio of the widest dimension to the narrowest dimension will be about 2.0.

Referring to FIG. 18, the overall dimensions of the upper composite material 103 portion of a healing abutment 119 indicates that one possible size is nominally about eight millimeters at the widest point, and six millimeters at the narrowest point. The size of the maximum dimension for the healing abutment 119 may vary between about five to about nine millimeters. The size of the minimum dimension for the healing abutment 119 may vary between four to about seven millimeters. The resulting maximum possible ratio of the widest dimension to the narrowest dimension is then about 2.25.

Referring to FIG. 19, the overall dimensions of the upper composite material 103 portion of a healing abutment 121 indicates that the size is nine millimeters at both the widest and narrowest perspectives. The size of the maximum dimension for the healing abutment 121 may vary between about seven to about ten millimeters. The size of the minimum dimension for the healing abutment 121 may vary between seven to about ten millimeters. The resulting maximum possible ratio of the widest dimension to the narrowest dimension is then about 1.4. The ranges of dimension which have applied to the healing abutments 101, 117, 119, and 121 will similarly apply to the associated shapes for the associated impression copings, collars, blanks and rough preparations to be hereinafter described. Only the nominal dimensions will again be given, and ranges stated above for the healing abutments will apply to each of those shapes following.

Referring to FIG. 20, a sectional view of an impression coping 125 of the present invention is shown. The impression coping 125 provides a tissue support structure which exactly matches the structures of the healing abutment 101, so that even for the several minutes necessary to take the impression, the tissues 31 are supported in the same manner as during healing. The impression coping 125 has a composite material lower section 127 and a metallic square or rectangular boss 129. All of the metal material in the impression coping 125 is preferably made of titanium. Optionally, it may have a screw extension tube similar to screw extension tube 71 sitting above the rectangular boss 129. The rectangular boss 129 insures that there will be proper orientation when an impression material is introduced simultaneously over the impression coping 125, first and second teeth 33 and 35, and over the section of human oral gum tissue 31.

Once the impression has been taken, the healing abutment 101 will be reintroduced into the space between the teeth 33 and 35 as shown in FIG. 12 while a dental lab performs the work necessary to form the tooth prosthesis. Because of the specific orientation of the lower composite material section 127, it is important that the impression coping 125 is keyed for rotational stability in the same manner as the healing abutment.

As can also be seen in FIG. 20, the impression coping 125 has a bore 131 which accommodates the elongate threaded screw 73 having head 72. The metallic portion of the impression coping 125 includes not only the rectangular portion 129 but also a neck portion 133 and a ribbed portion 135. The ribbed portion 135 carries a series of annularly spaced lands 137 which provide more bonding area for the lower composite material section 127 and to prevent axial removal of the composite material section 127. As in the case of the healing abutment, the composite material of the composite material section 127 is preferably a composite like resin which is generally described in dentistry as a composite resin that is either light (photo) cured or chemical cured, and may be tooth colored.

The impression coping 125 metallic portion also includes a metal portion 139 and a lower rim 141, and of which neck 133, ribbed portion 135, and series of annularly spaced lands 137 are an integrally formed part. The bore 131 of the metal portion 139 is of sufficient size to accommodate the elongate threaded screw 73, but an aperture at the bottom of the bore 131 prevents the elongate screw 73 from passing downward completely through the impression coping 125 so as to enable the healing abutment to be secured onto the bone implant 45. Within the lower rim 141, a twelve position depression 143 is carried to again permit 12 different positions to be achieved.

Other views of the healing abutment include FIG. 21 which illustrates a top view including an aperture 145 smaller than the bore 131 to secure the elongate threaded screw 73. As can be seen, the impression coping 125 at the composite material lower section 127 has a maximum width dimension of seven millimeters and a minimum width dimension of seven millimeters. Referring to FIG. 22, a plan view of the impression coping 125 illustrates the exterior surface features thereof.

Referring to FIG. 23, a bottom view of the impression coping 125 illustrates in greater detail the twelve position depression 143, as well as the overall curved triangular shape of the composite material lower section 127. Referring to FIG. 24, the overall dimensions of the composite material lower section 127 of an impression coping 129 indicates that the size is seven millimeters taken from both the widest and narrowest perspectives. Referring to FIG. 25, the overall dimensions of the composite material lower section 127 of impression coping 153 indicates that the size is eight millimeters at the widest point, and six millimeters at the narrowest point. Referring to FIG. 26, the overall dimensions of the composite material lower section 127 of an impression coping 155 indicates that the size is nine millimeters at both the widest and narrowest perspectives, and two corners of the rectangular shape are more sharply angled than the other two corners even though the sharply truncated corners still have a curved rather than abrupt transition.

Figure 27:
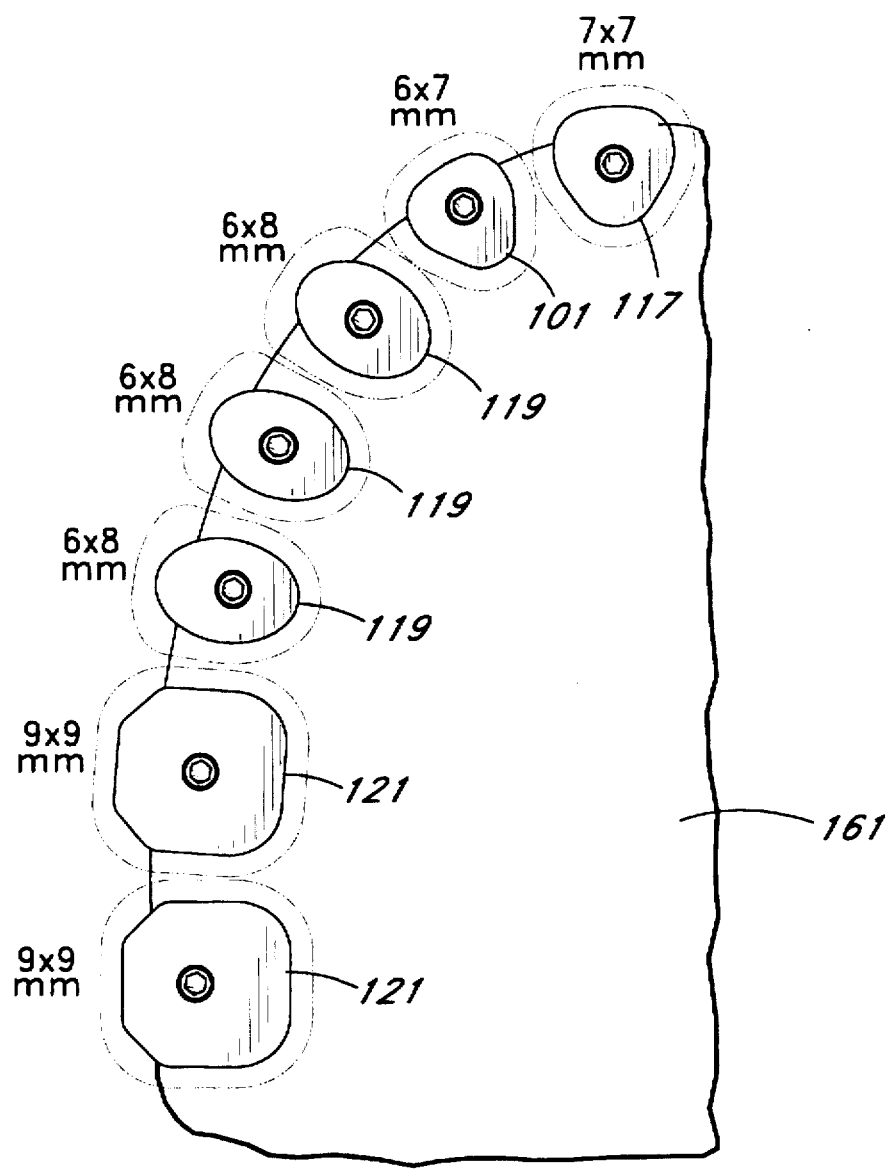
FIG. 27 is a view of the approximate position in the oral cavity in which each of the shapes of the healing abutments and impression copings of the present invention would be placed.

Referring to FIG. 27, a schematic view of one half of the tooth positions in a one half oral cavity section 161 illustrates the placement of the shapes shown for the healing abutments 101 and impression copings 125, even though only the healing abutments 101 are shown in FIG. 27. A central, large anterior tooth will preferably utilize the seven millimeter triangular healing abutment 117. A lateral smaller anterior tooth will preferably utilize the six millimeter by seven millimeter triangular healing abutments 101.

The cuspid and bicuspid teeth will preferably utilize the six millimeter by eight millimeter oval healing abutments 119, and three such abutments 119 are shown. Lastly, the molars will preferably utilize the nine millimeter square healing abutments 121, and two such abutments 121 are shown and will preferably be supported on a six millimeter diameter bone penetrating implant 45.

In the inventive system herein, not only do the healing abutments 101, 117, 119, and 121, and the impression copings 125, 151, 153, and 155 carry the same shape of composite material to support the gum tissue 31, but the tooth prosthesis in the present inventive system also carries the same shape. In this inventive system, the tooth prosthesis will occupy the same gum tissue 31 space and a volume occupied within the gum tissue exactly as was occupied by the healing abutments, 101, 117, 119, and 121.

Referring to FIG. 28, an exploded view of a tiered aesthetic prosthesis support 171 is illustrated over the standard bone implant 45 previously shown. From the top, the standard threaded screw 104 is still utilized in this embodiment. The next structure is a conical cup shaped coping 173 which is engaged by the threaded screw 104 in the downward direction. The conical cup shaped coping 173 varies in height from 2 millimeters to 7 millimeters in height. The conical cup shaped coping 173 provides an expanded surface area and angled surfaces to increase the holding surface provided for the material which will form the tooth prosthesis. The conical cup shaped coping 173 also has an upper overhanging lip 175 to further increase its holding power. The coping 173 also has hexagonal surfaces wo engage other hexagonal surfaces in order to enjoy a non-turnable, stable structure.

A fitting 177 is engaged by the threaded screw 104 and itself has a downwardly extending threaded extension 179. The upper portion of the fitting 177 also has a hexagonal shape which may engage similar shapes within the coping 173. Between the lower surface of the conical cup shaped coping 173 and the upper surfaces of the bone implant 45, a sized insert or interchangeable collar 181 is secured. The sized insert has a height h, and a shape matching the upper composite material 103 of healing abutment 101 and the lower composite material section 127 of the impression coping 125. The height h is preferably in the range of from one millimeter to about seven millimeters.

The collar 181 has hexagonal locking structure 182 in place atop the collar 181 and may form a portion or all of the material extending through the collar 181. As an alternative, the collar 181 and locking structure 182 could be integrally formed. In the alternative, the locking structure could be made of metal and occupy the internal portion of the collar so that the internal surfaces discussed below would be made of such metal material.

In the system of the present invention, the collar 181 represents the third identical sized and shaped structure which will face the healed gum tissue 31 so that the installation and use of the tooth prosthesis will also not serve to damage or re-injure the gum tissues 31. By using (1) a shape which approximates the space of the removed tooth and (2) a consistent shape throughout healing, impression taking, and fitting of the final implant tooth prosthesis, the gum tissue 31 will have greater support and better supported healing.

As is shown in FIG. 28, the collar 181 is provided independent of the fitting 177 and the conical cup shaped coping 173, although these portions of the structure could be supplied as an integrated piece. The sized collar 181 has a bore 183 extending therethrough, and the surface of this bore 183 could be metallic if metal is used for the core of the collar 181. The collar 181 has a lower twelve position depression 185, and an upper chamfer 187 to accommodate and engage an expanded portion 189 of the fitting 177. Depending upon the material used, the collar 181 could have an optional metallic rim 190 at the bottom of the collar 181. In this configuration, the rim 190, internals, including the surface of the bore 183, as well as the locking structure 182 could be made of metal to annularly externally hold and sandwich the composite portion of the collar 181 in place.

Referring to FIG. 29, the overall shape of the collar 181 is seen as matching the shape of and the dimensions of both the healing abutment 101 and the impression coping 125. Since FIG. 29 is a view taken along line 29—29 of FIG. 28, the downward viewpoint illustrates the chamfer 187, locking structure 182, as well as the bore 183. Referring to FIG. 30, a view taken along line 30—30 of FIG. 28 illustrates a closeup view of the twelve position depression 185 against the bore 183.

Likewise, referring to FIG. 31, an insert 189 has a shape and dimensional area matching healing abutment 117 and impression coping 151. Referring to FIG. 32, an insert 191 has a shape and dimensional area matching healing abutment 119 and impression coping 153. Referring to FIG. 33, an insert 193 has a shape and dimensional area matching healing abutment 121 and impression coping 155.

Referring to FIG. 34. The completed assembly of FIG. 28 is shown in place and with an overlay of porcelain material 195 (shown in phantom) forming the shape and size of the tooth prosthesis. The porcelain material 195 is typically affixed to and baked onto the cup shaped gold coping before it is attached to the other structures shown in FIG. 34. The porcelain material 195 contains a bore 197 to permit access to the threaded screw 104 to both secure and remove the entire tooth prosthesis, referred to with the numeral 199.

As mentioned above, the locking structure 182 is shown as being made of metal to annularly externally hold and sandwich the composite portion of the collar 181 in place. The metal portions of the collar 181 include the locking structure 182, the upper chamfer 187, bore 183, and lower twelve position depression 185.

Figure 35:
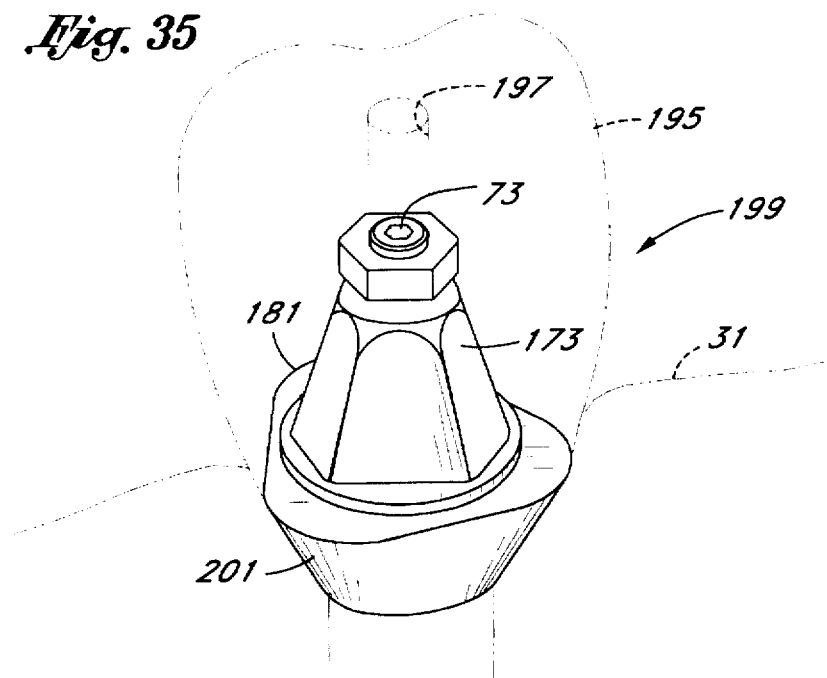
FIG. 35 is a perspective view of the assembled prosthetic tooth and prosthetic tooth support of FIG. 34 within schematically shown gum tissue and illustrating general orientation of the tooth prosthesis.
Figure 36:
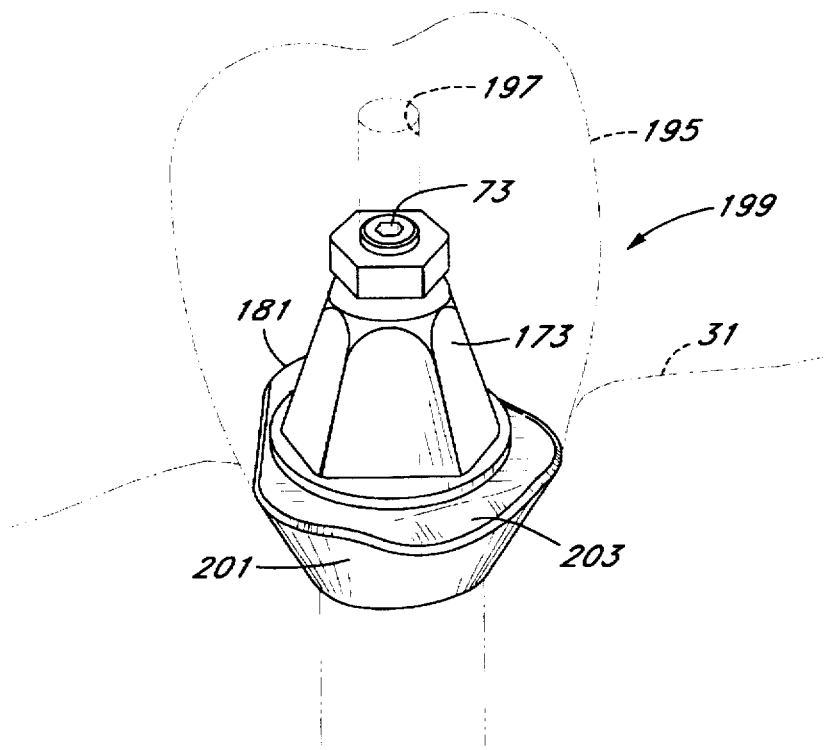
FIG. 36 is a perspective view of the assembled prosthetic tooth and prosthetic tooth support of FIG. 35 and showing a chamfer carved into the metal portion of the prosthesis to make room for additional porcelain to enable the level of the porcelain to extend below the top of the gum tissue.

Referring to FIG. 35, the tooth prosthesis 199 is shown in place with respect to the gum tissue 91, but shown without the presence of the other teeth 33 and 35. The porcelain material 195 extends downward to a flat surface of the sized collar 181. A front edge 201 of the collar 181 is, with respect to the gum tissue 31, oriented outward and away from the center of the oral cavity. Referring to FIG. 36, an illustration of how the collar 181 can have its outward front edge 201 ground down is illustrated. The front edge 201 has a custom shaped chamfer 203 to enable more of the porcelain 195 to dip lower into the area which would otherwise be occupied by the collar 181 material. This is useful where the top of the collar 181 would otherwise rise above the gum tissue 31. The chamfer 203 enables the porcelain material 195 to dip below the upper surface of the collar 181.

Referring to FIG. 37, another method of forming a tooth prosthesis is illustrated. Rather than having an interchangeable collar 181 on which a porcelain mass is attached, this method involves beginning with a cup-shaped annular mass of titanium whose bottom portion has shapes which already conform to the shapes of the healing abutments 101, 117, 119, and 121, and the impression copings 125, 151, 153, and 155 already discussed above. A porcelain cap could then be attached to the upper surface of the mass after formation, for aesthetic purposes. An important advantage to be gained is in processing. Here the tooth prosthesis, except perhaps for the upper cap, can be formed by standard dental drill sculpting techniques in the dental lab.

Referring to FIG. 38, a top view of a single root form dental prosthesis blank 211 is shown. A bore 213 extends through the length of the blank 211, restricted at the lower end by a reduced inner diameter neck 215. The blank 211 has an upper surface 217.

Referring to FIG. 38, the blank 211 is initially about 9 millimeters tall. As can be seen from the side view with dashed line detail, the bottom of the blank 211 contains a twelve position depression 219. The transition from the bore 213 to the depression 219 is through an angled internal surface 221 leading to the reduced inner diameter neck 215 and then to the depression 219. Referring to FIG. 39, a bottom view of the blank 211 shows greater details of the depression 219.

Referring to FIG. 40, a sectional view of the blank 211 assembled over the bone implant 45 illustrates the mode of fit, and includes the securing of the blank 211 to the implant 45 by the threaded screw 104 which passes through a bore 214. A portion of the lower radial surface of the blank 211 is identified with a bracket numbered 223 to emphasize that this portion of the lower external surface should match the external surfaces of the portions of the healing abutments 101, 117, 119, and 121, and the impression copings 125, 151, 153, and 155 which would extend below the uppermost level of the gum tissue 31. So long as this requirement is met, it makes little difference which shape the blank assumes above the bracketed portion 223 since the blank 211 is intended to be significantly sculpted into another shape.

Top views of other blanks are illustrated which related to the other shapes of the healing abutments 101, 117, 119, and 121, and the impression copings 125, 151, 153, and 155 and the collars 181, 189, 191, and 193 which were earlier shown. FIG. 41 illustrates a blank 231. FIG. 43 illustrates a blank 233, and FIG. 45 illustrates a blank 235. Blanks 211, 231, 233, and 235 correspond to the shape of the healing abutments 101, 117, 119, and 121, and the impression copings 125, 151, 153, and 155 and the collars 181, 189, 191, and 193, as ordered respectively.

As an alternative to the provision of a blank such as blank 211, a series of pre-formed shapes also known as rough preparations may be provided to prevent the dental lab technicians from having to start from scratch in forming the final shapes which the blank 211 will assume. Referring to FIG. 44, the first of a series of rough preparations are shown, each of which have the same internal shapes as did the blank 211.

At FIG. 44, a rough preparation 251 has an of inside directed groove surface 253 and an outside directed groove surface 255 separated from said inside directed groove surface 253 by a pair of angled transitions. Rough preparation 251 is for the anterior teeth. Above the groove surfaces 253 and 255 are an outside round surface 257 and an inside swept triangular surface 259. Also seen is a top angled surface 261. FIG. 45 illustrates a top view of the rough preparation 251 while FIG. 46 illustrates its bottom view.

Referring to FIG. 47 the rough preparation 251 is shown in place surrounded by gum tissue 31 and having a layer of baked porcelain 265 overlying the upper portion of the rough preparation 251. Not shown in FIG. 47, for simplicity, are the remainder of the structure which would be present to hold the rough preparation 251 in place. It is understood that the rough preparation may be further sculpted in the dental lab, but that the rough preparation will simply save time, perhaps in giving a head start to the time spent on overall formation.

Referring to FIG. 48, a rough preparation 271 for a bicuspid prosthesis has an outside directed groove surface 273 and an inside directed groove surface 275 separated by smooth upward transition. Above the groove surfaces 273 and 275 are an outside round surface 277 and a top rolling slope surface 279. Also shown are a pair of retentive grooves 280 which aid in holding the porcelain prosthesis.

FIG. 49 illustrates a top view of the rough preparation 271 while FIG. 50 illustrates its bottom view.

Referring to FIG. 51 the rough preparation 271 is shown in place surrounded by gum tissue 31 and having a layer of baked porcelain 281 overlying the upper portion of the rough preparation 251. Again, not shown are further details of the internals of rough preparation 251 for simplicity sake.

Referring to FIG. 52, a rough preparation 291 for a molar prosthesis has an outside directed groove surface 293 and an inside directed groove surface 295 separated by smooth upward transition. The corners of the outside directed portion of the overall rough preparation 291 are more sharply angled than the inside directed portion. Above the groove surfaces 293 and 295 is a top rolling slope surface 297. Also seen are a pair of retentive grooves 299. FIG. 53 illustrates a bottom view of the rough preparation 291.

Referring to FIG. 54 the rough preparation 291 is shown in place surrounded by gum tissue 31 and having a layer of baked porcelain 281 overlying the upper portion of the rough preparation 291. Again, not shown are further details of the internals of rough preparation 251 for simplicity.

While the present invention has been described in terms of a dental implant system and method for facilitating the use of a constant shape to promote healing and prevent damage, one skilled in the art will realize that the structure and techniques of the present invention can be applied to many similar devices. The present invention may be applied in any situation where a series of structures are required for healing/formation, casting, and permanent structure introduction.

Although the invention has been derived with reference to particular illustrative embodiments thereof, many changes and modifications of the invention may become apparent to those skilled in the art without departing from the spirit and scope of the invention. Therefore, included within the patent warranted hereon are all such changes and modifications as may reasonably and properly be included within the scope of this contribution to the art.

What is claimed:

1. An impression coping comprising: an elongate cylindrical body extending about a central axis and having a first end and a second end, said second end having a radial plate extending in a direction perpendicular to said central axis and defining a small aperture at the radial center of said radial plate, a radially grooved section adjacent said radial plate and having a series of spaced radial grooves and distributed in the direction of said first end, a smooth section adjacent the radially grooved section, and a radially expanded section extending from said smooth section to said first end, said elongate cylindrical body defining a central bore extending along said central axis and having an internal diameter greater than said small aperture and in open communication with said small aperture; and a mass of composite material supported by said radial plate and said series of spaced radial grooves and having when viewed from an axial direction, an acylindrical shape.

2. The impression coping of claim 1 wherein said composite material has a generally tapering shape, with a smaller diameter of said tapering shape adjacent said radial plate and a relatively larger diameter of said tapering shape located away from said radial plate.

3. The impression coping of claim 1 wherein said acylindrical shape is a rounded triangular shape.

4. The impression coping of claim 3 wherein said rounded triangular shape has a ratio of maximum to minimum diameter of from about 1.0 to about 2.0.

5. The impression coping of claim 1 wherein said acylindrical shape is an oval shape.

6. The impression coping of claim 1 wherein said acylindrical shape is a rounded rectangular shape.

7. The impression coping of claim 6 wherein said rounded rectangular shape has two adjacent corners which are more sharply angled than another two adjacent corners.

8. The impression coping of claim 1 wherein the surface of said radial plate disposed away from said second end of said elongate acylindrical body has a hexagonally compatible depression centered about said central axis.

9. A healing abutment comprising: an elongate cylindrical body extending about a central axis and having a first end and a second end, said second end partially closed but for an aperture at the radial center of said second end, a externally radially grooved section on the exterior of said elongate cylindrical body and having a series of spaced radial grooves, and a radially expanded rim section adjacent said second end, said second end defining an outwardly directed and mutually inwardly disposed hexagonally compatible depression; and a mass of composite material supported by said radially expanded rim and said series of spaced radial grooves and having when viewed from an axial direction, an acylindrical shape.

10. The healing abutment of claim 9 wherein said acylindrical shape is a rounded triangular shape.

11. The healing abutment of claim 10 herein said rounded triangular shape has a ratio of maximum to minimum diameter of from about 1.0 to about 2.0.

12. The healing abutment of claim 9 wherein said acylindrical shape is an oval shape.

13. The healing abutment of claim 9 wherein said acylindrical shape is a rounded rectangular shape.

14. The healing abutment of claim 13 wherein said rounded rectangular shape has two adjacent corners which are more sharply angled than another two adjacent corners.

15. The healing abutment of claim 13 wherein said rounded rectangular shape has two adjacent corners which are more sharply angled than another two adjacent corners.

16. The healing abutment of claim 9 wherein said composite material has an exterior generally tapering shape, with a smaller average diameter of said tapering shape adjacent said second end of said elongate cylindrical body.

17. The healing abutment of claim 9 wherein said composite material has flat surface, disposed in an axial direction, immediately adjacent said first end of said elongate acylindrical body.

18. A tooth prosthesis support comprising:

an interchangeable collar having a tapering shape having a first end of a relatively larger diameter than a second end and having a bore extending therethrough and an outwardly directed and mutually inwardly disposed hexagonally compatible depression at said second end, and surrounding said bore, a fitting having a threaded bore in a first end and having an externally disposed thread at said second end fittable through said bore;

a threaded screw having a head and a threaded body;

a conical cup shaped coping having an aperture fittable over and securable to the first end of said fitting by the insertion of said threaded body of said threaded screw through said aperture of said conical cup shaped coping, said conical cup shaped coping having a lower rim abutting said first end of said interchangeable collar; and a mass of baked porcelain extending over the cup shaped coping and atop the interchangeable collar and defining an access bore through which said threaded screw may have access to said aperture of said cup shaped coping.

19. The tooth prosthesis support of claim 18 wherein said interchangeable collar has a rounded corner triangular shape.

20. The tooth prosthesis support of claim 18 wherein said interchangeable collar has an oval triangular shape.

21. The tooth prosthesis support of claim 18 wherein said interchangeable collar has a rounded corner rectangular shape.

22. A tooth prosthesis support comprising:

a tapering body having a first end and a second end and having a first bore along a central axis, said first bore having a first end opening to said first end of said tapering body and a second end, a second bore having a first end nearer said first end of said tapering body than said second end of said tapering body, a conical transition surface extending between said second end of said first bore and said first end of said second bore, and a hexagonally compatible depression surrounding said second end of said second bore and, when said tapering body is viewed from an axial direction, an anatomical tooth shape, said tapering body having an inside directed groove surface and an outside directed groove surface which meets said inside directed groove surface at a pair of angled transitions, and wherein the upper surface of said tapering body is flatly sloped.

23. The tooth prosthesis support as recited in claim 22 and further including a curved triangular transition surface adjacent said flatly sloped upper surface.

24. The tooth prosthesis support as recited in claim 22 and further including an inside directed groove surface and an outside directed groove surface which meets said inside directed groove surface along a pair of smooth upward transitions, and wherein the upper surface of said tapering body has a rolling slope surface.

25. The tooth prosthesis support as recited in claim 22 and further including an inside directed groove surface and an outside directed groove surface which meets said inside directed groove surface along a pair of smooth slightly upward transitions, and wherein the upper surface of said tapering body has a pair of oppositely disposed sloped surfaces sloped toward a line extending across the axial center of said tooth prosthesis support.

* * * * *